United States Patent [19]

Hofmann

[11] Patent Number: 5,194,252
[45] Date of Patent: Mar. 16, 1993

[54] MOISTURE RETAINING AFTERSHAVE

[75] Inventor: William H. Hofmann, St. Louis, Mo.

[73] Assignee: ViJon Laboratories, Inc., St. Louis, Mo.

[21] Appl. No.: 819,369

[22] Filed: Dec. 31, 1991

Related U.S. Application Data

[63] Continuation-in-part of Ser. No. 555,786, Jul. 19, 1990, Pat. No. 5,077,038, and a continuation-in-part of Ser. No. 386,304, Jul. 27, 1989, abandoned.

[51] Int. Cl.$^5$ .......................... A61K 7/06; A61K 7/15
[52] U.S. Cl. ..................................... 424/73; 424/70; 424/74; 514/844; 514/846; 514/847; 514/873; 514/880; 514/944; 514/975
[58] Field of Search ............................ 424/61, 73, 74

[56] References Cited

U.S. PATENT DOCUMENTS

| 4,128,631 | 12/1978 | Landmark et al. | 424/70 |
| 4,485,037 | 11/1984 | Curtis | 252/546 |
| 4,735,798 | 4/1988 | Bernstein | 424/61 |
| 4,824,662 | 4/1989 | Hofmann | 424/61 |
| 5,077,038 | 12/1991 | Hofmann | 424/61 |

Primary Examiner—Thurman K. Page
Assistant Examiner—James M. Spear
Attorney, Agent, or Firm—Edward H. Renner

[57] ABSTRACT

A novel composition of a hydrolyzed protein together with a surfactant produces a proteinaceous film on the skin to retard moisture loss in cosmetic and toiletry products, such as after shaves, and cleansing lotions. The products retard moisture loss from the skin matrix, but the primary cleansing functions of the products, i.e., removing excess moisture and oil, are not inhibited.

5 Claims, No Drawings

MOISTURE RETAINING AFTERSHAVE

BACKGROUND AND SUMMARY OF THE INVENTION

This application is a continuation-in-part of U.S. patent applications Ser. No. 07/555,786, filed July 19, 1990, now U.S. Pat. No. 5,077,038; and Ser. No. 07/386,304, filed July 27, 1989, now abandoned.

U.S. Pat. No 4,824,662, of which I am the inventor, relates to a novel nail polish remover composition developed to minimize the dehydrating effects on the skin and nails of the solvents necessary to soften and dissolve nail lacquer. U.S. Pat. No. 5,077,038 also relates to nail polish removers which minimize the dehydrating effect on the skin. I am also aware of U.S. Pat. Nos. 4,128,631, 4,485,037 and 4,735,798. The disclosures of the above U.S. patents and patent application are incorporated by reference herein.

Other cosmetic products, such as aftershave lotions and cleansing lotions, normally contain solvents, such as alcohol. These solvent containing products are applied to the skin and usually display some degree of dehydrating of the skin. A particular function of some aftershave and cleansing lotions is to cleanse the skin and remove excess moisture and oil. This cleansing function can lead to even greater loss of moisture with attendant drying of the skin due to the greater time during which the solvent remains in contact with the skin.

As was disclosed in the U.S. Pat. No. 4,824,662, the addition of specified amounts of a cosmetically acceptable amidoamine salt of hydrolyzed soy protein having a molecular weight of about 1000–4000, and a surfactant, such as cocamidopropyl dimethylamine propionate, function to minimize the dehydrating effects of the solvents in nail lacquer removal. This effect of nail lacquer removal occurs by solvent extraction of oils from the skin matrix into the solution of solvents in the lacquer remover. The soy and surfactant additives reduce the extraction potential of the solvent solution. However, it was believed that such soy and surfactant material could not be effective anti drying agents in products, such as aftershave and cleansing lotions, where the primary function of the material is to cleanse the skin and remove excess oil and water. The anti-drying additives were believed to inhibit this primary function. Further, products such as aftershave lotions may remain in contact with the skin for a greater time, usually until complete evaporation occurs, providing more time for the solvents to dry the skin matrix. It has been found, however, that an unexpectedly high degree of anti-drying can be achieved in a suitably prepared aftershave or cleansing lotion and still maintain the primary function of the material. The effect can be obtained by producing a film on the skin which contains the anti-drying additives. Other materials, such as lubricants, can be included in the film.

It is thus an object of the invention to produce a composition which is effective to reduce the moisture and oil loss from the skin matrix caused by the application of solvent containing dermal preparations.

It is a further object of the invention to reduce the drying effect of the skin matrix caused by the topical application of skin cleansing materials containing solvents.

It is a further object of the invention to inhibit the drying effect and oil removing effect on the skin matrix found in solvent containing aftershaves and cleansing lotions.

It is a further object of the invention to provide a dermal material for topical application which provides a lubricating and protective function to the skin.

It is a further object of the invention to provide a material for application to the skin which provides an anti-irritant and moisture retaining film.

It is a further object of the invention to produce a moisture retaining and anti-irritant material which contains hydrolyzed soy protein materials which are compatible with a solution of aqueous alcohol.

It is a further object of the invention to produce a material for topical application to the skin which will cleanse and remove excess moisture and oil from the surface of the skin yet provide a protective effect to retain the moisture and oil in the skin matrix.

It is a further object of the invention to produce a film forming moisture retaining preparation for application to the skin which contains cosmetically effective amounts of hydrolyzed soy protein and cosmetically effective amounts of a surfactant material.

Further objects of the invention will be apparent from the following Description of the Preferred Embodiments and Examples.

DESCRIPTION OF THE PREFERRED EMBODIMENTS

Soy protein hydrolysate are relatively new materials for us in cosmetic preparations. They are made from either a soy isolate, a relatively pure plant derived protein extracted from soy beans, or, from a soy flour which is made by crushing soy beans and extracting the protein present during the hydrolysis process. Soy beans contain roughly 40% protein and 40% carbohydrate (polysacchride) and 20% oil. Soy bean isolate, the preferred starting material, has the oil and polysaccharide materials removed, is extracted from soy flour by a complex washing process which separates the protein from the polysacchride materials. The oil is removed in a prior solvent extraction.

It is important in cosmetic ingredients which have to be light in color and low in odor, to remove all the polysaccharide materials, otherwise they will react with the terminal amino groups present in the soy protein giving rise to the Maillard reaction. When this happens dark brown odiferous products are formed which are, generally speaking, highly undesirable in cosmetic products. Hence, it is preferred that a pure soy protein isolate is used.

Soy protein hydrolysate made from soy protein isolates are excellent conditioning materials for the skin, hair and nails (any keratinized body surface layer) as they form moisture retentive films which will help the substrate hold more moisture than it would normally. Soy proteins contain all the essential amino acids and represent a completely balanced product from a nutritional viewpoint. Commonly used cosmetic proteins are normally collagen based and collagen is deficient in the essential amino acid tryptophane. For healthy skin, hair and nails it is necessary to use products with a complete complement of essential amino acids, as found in soy proteins.

I have found that hydrolyzed soy proteins, when topically applied as films, have the following beneficial properties to the skin and hair:

a) It forms smoothing films, helping to minimize roughness and wrinkles.
b) It will have a protective colloid effect.
c) It forms a moisture retentive film on the surface of the skin which will help plump "normal" dry skin, improving its elasticity and suppleness.
d) It combats chapping and irritation caused by detergents.
e) It forms a moisture retentive film which will increase the moisture content of the skin, improving flexibility.
g) It protects, through the protective colloid effect, the skin from environmental damage (pollutants, soap, cleansing compounds) which will remove the essential cementing lipids in the matrix from the skin keratin.

It has been found that the foregoing properties are present to an optimum degree in a hydrolyzed soy protein with an average molecular weight of about 1,000–4,000.

Hydrolyzed soy proteins hereinbefore described are water soluble (or water dispersible) and compatible with up to 50% aqueous alcohol. To achieve compatibility with aqueous ethanol solutions, a further processing step, amidization of the protein is required. This can be substantially represented by the following formula:

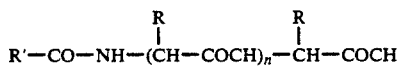

R' = Fatty Acid of 5–22 carbons (preferably isostearic acid - 18 carbons)
R = Side-chain groups characteristic of amino acids in soy protein
n = Integer from 10 to 40

The conversion of accessible primary amine groups of hydrolyzed soy protein (including the sidechain or epsilon amino groups, such as arginine and lysine—a key essential amino acid) to amide groups, imparts an anionic charge to the hydrolyzed soy protein. This enables it to form stable salts with bases: organic amines, such as alkyl and hydroxyalkyl amines of 1–4 carbons atoms, e.g., trimethylamine, diethylamine, etc.; and alkanolamines of 1–4 carbon atoms, such as ethanolamine, propanolamine, aminomethylpropanol, etc. The exact nature of the amine which forms the salt is not critical, as long as the salt formed is cosmetically acceptable and is soluble in aqueous ethanol.

The preferred product is a salt of a fatty acid amide of hydrolyzed soy protein, i.e., the aminomethylpropanol salt of isostearic amide of hydrolyzed soy isolate protein. A suitable product of this type is available from Brooks Industries, Inc., 70 Tyler Place, South Plainfield, N.J. 07080, under the trademark of ETHA-SOY ISO as a light yellow clear liquid with a solids content of 27–35% (after drying for 16 hours at 105° C.), a pH 7.0–9.5 (10% aqueous solutions at 25° C.), a specific gravity of 0.830–0.880 (at 25° C.), and an acid value of 35.0–50.0.

The presence of this derivative of hydrolyzed soy protein, in conjunction with the amidoamine salt, will substantially reduce the propensity of the solvent (ethanol solutions) to remove water from the skin of the user. In particular, the combination in sufficient concentration imparts a film on the skin which retains moisture in the skin matrix to an unexpected high degree. This film is superior to that produced by either ingredient alone. Moreover, the film does not inhibit removal of surface moisture and oil to any significant degree.

The combination of the above described derivative of hydrolyzed soy protein is further enhanced by the presence, in solution of a surfactant will substantially reduce the propensity of the solvent (aqueous ethanol) to remove water from the skin of the user.

The preferred surfactant for this system is (but not limited to) cocamidopropyl dimethylamine propionate, which is described as the propionic acid salt of cocamidopropyl dimethylamine (q.v.) it conforms generally to the formula:

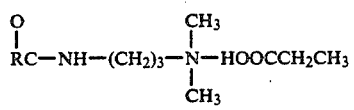

where RCO represents the coconut acid radical. A suitable product of this type is available from McIntyre Chemical Company, 4851 S. St. Louis Avenue, Chicago, Ill. 60632 under the trademark of MACKALENE 117.

Generally, a suitable cleansing material, such as an aftershave lotion, will contain solvents, such as ethanol, isopropyl alcohol and water. The solvent will contain various fragrances, cleaning agents and skin protective materials dissolved or dispersed in the solvent. The aftershave may exist as a liquid, a gel or semi-gel. A preferred composition may contain from about 0–70% alcohol; about 25–80% water, depending on the form of the lotion. Likewise, suitable cosmetically acceptable fragrances, fixatives, such as the bezophenones, and dyes may be included, as is known in the art. These dyes and fragrances will typically be included in proportions of between about 0.5 to 4% by weight, for fragrances, and up to about 0.5% for dyes. Also included are various surfactants and dispersants. The dispersants function to maintain a stable solution or dispersion between the aqueous and non-aqueous portions of the cleansing preparation. The surfactants provide cleansing properties to the lotion as well as assisting in maintaining a stable solution or dispersion. Various cosmetically acceptable germicides and preservatives may be included, as desired, and plasticizers and skin conditioners to assist in maintaining the film forming and skin anti-drying properties. Suitable germicides include quaternary amines such as QUARTERNIUM (TM) compounds, allantoin and the like. Suitable plasticizers include glycerin, propylene glycol, glycerides and the like. Skin conditioners may include the siloxane conditioners, such as DIMETHICONE (TM) and CYCLOMETHICONE (TM) and vitamins such as panthenol. If a gel type lotion is desired, various gel forming agents may be added, such as fatty acid salts (soaps) and esters, such as the PEG (TM) surfactant esters and film forming polymers such as carbomers including CARBOPOL (TM) and the like. In particular, the combination of hydrolysed soy protein, surfactant and plasticizer form a particularly effective film forming material which conditions the skin and retains moisture and flexibility in the skin without inhibiting the primary skin cleansing function of the lotion. Various amine compounds, such as EDTA, THPEA, TEA and the like may be added for stability. Also various extracts, such as witch hazel, aloe and the like may be added to give an astingent character and characteristic fragrance. Typically a lotion according to this invention will include from about 0–10% plasticizers, from about 0–5% gel forming salts and esters, from about 0 to 1% germicides, from about 0 to 1% skin conditioners and from about 0 to 3% astringents. Amine neutralizers and stabilizers may be present from about 0 to 1%. All percentages are given by weight.

The invention may be further understood by reference to the following Examples:

EXAMPLE I

All proportions are expressed as % by weight.

A clear aftershave was prepared, having the following composition:

| | |
|---|---|
| SD Alcohol 40-2/B | 52.35 |
| Fragrance | 1.655 |
| Propylene Glycol | 2.0 |
| AMP Isostearic Hydrolyzed Soy Protein | 0.05 |
| Cocamidopropyl Dimethylamine Proprionate | 0.25 |
| Aloe Vera Gel | 0.75 |
| FD&C/D&C Dyes | Trace |
| Deionized Water | Q.S. |
| | 100 |

In preparation, the fragrance and soy protein are dissolved in the alcohol. The alcohol solution is covered tightly to retard evaporation and allowed to age. The water soluble ingredients are dissolved in the deionized water and mixed until clear. The alcohol solution is added gradually to the water phase with mixing. The combined solutions are mixed until clear and uniform. The mixed final product is sampled and tested against specifications then filtered and filled into bottles.

EXAMPLE II

All examples are expressed as % by weight.

An opaque gel type aftershave was prepared, having the following composition:

| | |
|---|---|
| SD Alcohol 40-2/B | 15.0 |
| Carbopol 934 | 0.3 |
| Allantoin | 0.10 |
| Fragrance | 0.5 |
| PEG-8 Distearate | 3.5 |
| PEG-2 Myristal Ether Proprionate | 0.5 |
| PEG-2 Stearate | 0.5 |
| AMP Isostearic Hydrolyzed Soy Protein | 0.05 |
| Cocamidopropyl Dimethylamine Propionate | 0.25 |
| Triethanol Amine | 0.25 |
| D&C/FD&C Dyes | Trace |
| Water | Q.S. |
| Preservatrives | Trace |
| | 100 |

In preparation, the Carbomer is gradually added to a portion of the formula water with moderate speed agitation and mixed until completely dispersed.

The balance of the formula water is added to a separate stainless steel steam jacketed manufacturing tank. Moderate mixing is started as the solution is heated to 60°–65° C. To the heated water the proprionate surfactant, dyes, preservatives, PEG-8 Distearate and PEG-2 Stearate are added and mixed until all materials are in solution. The heating is stopped and the Carbomer slurry added and mixed until completely dispersed. The neutralizer (TEA) is dissolved in water and added to the batch and mixed until a uniform gel is formed.

In a separate stainless steel container the SD Alcohol, fragrance and Soy Protein are added and mixed until uniform. When the aqueous batch temperature drops below 40° C. the alcohol phase is added and mixed until uniform. The batch is sampled, evaluated against specification and filled into containers.

EXAMPLE III

All proportions are expressed as % by weight.

An opaque non-alcohol aftershave conditioner was prepared, having the following composition:

| | |
|---|---|
| Glycerin | 3.0 |
| Carbopol 934 | 0.41 |
| Aloe Vera | 0.50 |
| Dimethicone | 0.10 |
| Cyclomethicone | 0.10 |
| Cocamidopropyl Dimethylamine Propionate | 0.25 |
| AMP Isostearic Hydrolyzed Soy Protein | 0.05 |
| Fragrance | 0.65 |
| PEG-60 Almond Glycerides | 1.0 |
| Triethanolamine | 0.1634 |
| Preservatives | 0.20 |
| D&C/FD&C Dyes | 0.00062 |
| Water, Deionized | 93.22 |
| Panthenol | 0.25 |
| | 100 |

This formula is made up of several distinct slurries.

1) A water soluble preservative is dissolved in a portion of the formula water. With high speed mixing the Carbomer is gradually added and mixed until smoothly dispersed.
2) The Aloe Vera, Panthanol and propionate surfactant are dissolved in the glycerin with adequate agitation.
3) The fragrance, silicones, oil soluble preservatives and Soy Protein are dispersed in the PEG-60 Almond Glycerides.
4) The balance of the formula water is added to a manufacturing tank and mixing started. Dyes are added and mixed. Next the Carbomer slurry is added and mixed—followed by the glycerin slurry and then the fragrance mixture. This is all mixed until uniform.
5) The neutralizer (TEA) is mixed with a small amount of water and dissolved.
6) With adequate mixing the neutralizer solution is added to the batch and mixed until uniform. The batch is sampled and tested against specification and then packaged.

EXAMPLE IV

All proportions are expressed as % by weight.

An clear conditioning aftershave conditioner was prepared, having the following composition:

| | |
|---|---|
| SD Alcohol | 52.0 |
| Glycerin | 1.50 |
| Aloe Vera Gel | 1.0 |
| Witch Hazel | 0.65 |
| Fragrance | 1.20 |
| AMP Isostearic Hydrolyzed Soy Protein | 0.05 |
| Cocamidopropyl Dimethyl Propionate | 0.25 |
| FD&C Dyes | Trace |

-continued

| | |
|---|---|
| Deionized Water | Q.S. |
| | 100 |

The batch mixing procedure is similiar to Example I with the two phases:
1) SD Alcohol, Soy Protein, Witch Hazel, Fragrance,
2) Deionized Water, Glycerin, Aloe Vera Gel, Proprionate surfactant and Dyes.

EXAMPLE V

All proportions are expressed as % by weight.

A clear gelled after shave product whose film forming properties retard moistures loss and extends fragrance duration was prepared having the following composition:

| | |
|---|---|
| SD Alcohol | 60.0 |
| Fragrance | 2.0 |
| PEG 60 Hydrogenated Castor Oil | 0.25 |
| Carbopol 934 | 0.588 |
| Disodium EDTA | 0.005 |
| AMP Isostearic Hydrolyzed Soy Protein | 0.05 |
| Cocamidopropyl Dimethylamine Proprionate | 0.25 |
| Quaternium-15 | 0.006 |
| Benzophenone 4 | 0.006 |
| FD&C Dyes | Trace |
| Tetrahydroxypropyl Ethylenediamine | 0.50 |
| Deionized Water | Q.S. |
| | 100 |

This formula is manufactured in distinct phases:
1) A Carbomer slurry is made using Deionized Water, Disodium EDTA, Carbomer, Quaternium-15, Benzophenon-4 and mixed until completely smooth and lump free.
2) The SD Alcohol, fragrance, PEG-60 Hydrogenated Castor Oil and Soy Protein are combined, mixed until clear and covered to age.
3) The bulk of formula water is charged into the manufacturing tank and the dyes are dissolved with the proprionate. With adequate agitating the Carbomer slurry is added and mixed until uniform. The SD Alcohol/fragrance mixture is then added and mixed until clear and uniform.
4) The neutralizer (Tetrahydroxypropyl Ethylenediamine) is dissolved in water and mixed until uniform.

Avoiding the formation of a vortex, the combined batch is mixed and the neutralizer solution is added. Mixing is continued until the batch is uniform. The batch is then sampled and evaluated against specification. The batch may then be packaged.

It will be understood by those skilled in the art that various changes and modifications may be made to the invention disclosed herein without departing from the spirit of the invention. The invention is not to be limited to the examples given herein for purpose of illustration, but only by the scope of the appended claims and their equivalents.

I claim:

1. A topical skin cleansing aftershave preparation having oil removing solvents consisting essentially of a skin cleansing base having active ingredients selected from the group consisting of ethanol, isopropyl alcohol, water and mixtures thereof and skin cleansing surfactant materials, the preparation having from about 0.05 to about 0.25% by weight of a cosmetically acceptable salt of a hydrolyzed soy protein having a molecular weight of between about 1000-4000, and from about 0.1 to 0.3% by weight of a cocoamidopropyl dimethylamine propionate, the preparation further containing a film plasticizer selected from the group consisting of glycerin, propylene glycol and cosmetically acceptable glycerides, the combination being effective to cleanse the skin without excessive oil removal and drying of the skin tissue.

2. A topical skin cleansing aftershave preparation having oil removing solvents consisting essentially of a skin cleansing base having active ingredients selected from the group consisting of ethanol, isopropyl alcohol, water and mixtures thereof and skin cleansing surfactant materials, the preparation having from about 0.05 to about 0.25% by weight of a cosmetically acceptable salt of a hydrolyzed soy protein having a molecular weight of between about 1000-4000, and from about 0.1 to 0.3% by weight of a cocoamidopropyl dimethylamine propionate, the preparation further containing a film plasticizer selected from the group consisting of glycerin, propylene glycol and cosmetically acceptable glycerides, the combination being effective to cleanse the skin without excessive oil removal and drying of the skin tissue and wherein the aftershave lotion is a gel.

3. A topical skin cleansing aftershave preparation having oil removing solvents consisting essentially of a skin cleansing base having active ingredients selected from the group consisting of ethanol, isopropyl alcohol, water and mixtures thereof and skin cleansing surfactant materials, the preparation having from about 0.05 to about 0.25% by weight of a cosmetically acceptable salt of a hydrolyzed soy protein having a molecular weight of between about 1000-4000, and from about 0.1 to 0.3% by weight of a cocoamidopropyl dimethylamine propionate, the preparation further containing a film plasticizer selected from the group consisting of glycerin, propylene glycol and cosmetically acceptable glycerides, the combination being effective to cleanse the skin without excessive oil removal and drying of the skin tissue and wherein the preparation contains a skin conditioner.

4. A topical skin cleansing aftershave preparation having oil removing solvents consisting essentially of a skin cleansing base having active ingredients selected from the group consisting of ethanol, isopropyl alcohol, water and mixtures thereof and skin cleansing surfactant materials, the preparation having from about 0.05 to about 0.25% by weight of a cosmetically acceptable salt of a hydrolyzed soy protein having a molecular weight of between about 1000-4000, and from about 0.1 to 0.3% by weight of a cocoamidopropyl dimethylamine propionate, the preparation further containing a film plasticizer selected from the group consisting of glycerin, propylene glycol and cosmetically acceptable glycerides, the combination being effective to cleanse the skin without excessive oil removal and drying of the skin tissue and wherein the preparation contains a germicide.

5. An aftershave lotion for conditioning and cleansing the skin, the lotion containing skin cleansing agents normally capable of drying oil and moisture from the matrix of the skin, including alcohol, the lotion active ingredients including those selected from the group consisting of ethanol, isopropyl alcohol, water, and mixtures thereof, the preparation also containing from about 0.05 to about 0.25% by weight of a cosmetically acceptable salt of a hydrolyzed soy protein having a molecular weight of between about 1000–4000, and from about 0.1 to 0.5% by weight of a cocoamidopropyl dimethylamine propionate, the combination of hydrolyzed soy protein and cocoamidopropyl dimethylamine propionate being between about 0.1 and 0.5% by weight, the aftershave lotion further containing up to about 1% germicides, up to 1% skin conditioners and up to about 10% of a film plasticizer selected from the group consisting of glycerin, propylene glycol, and cosmetically acceptable glycerides, the combination being effective to form a moisture and oil retaining film on the skin surface to retain moisture and oil in the skin matrix without inhibiting the cleansing function of the preparation.

* * * * *